US009763785B2

(12) United States Patent
Styrc (10) Patent No.: US 9,763,785 B2
(45) Date of Patent: Sep. 19, 2017

(54) DEVICE FOR PLACING A SEAL AROUND AN IMPLANT IN A BLOOD CIRCULATION PASSAGE, AND ASSOCIATED TREATMENT KIT

(71) Applicant: CORMOVE, Irvy-le-Temple (FR)

(72) Inventor: Witold Styrc, Kopstal (LU)

(73) Assignee: CORMOVE, Ivry-le-Temple (FR)

( * ) Notice: Subject to any disclaimer, the term of this patent is extended or adjusted under 35 U.S.C. 154(b) by 19 days.

(21) Appl. No.: 14/693,122

(22) Filed: Apr. 22, 2015

(65) Prior Publication Data

US 2015/0305869 A1 Oct. 29, 2015

(30) Foreign Application Priority Data

Apr. 24, 2014 (FR) ...................................... 14 53699

(51) Int. Cl.
*A61F 2/24* (2006.01)
*A61F 2/01* (2006.01)

(52) U.S. Cl.
CPC ............ *A61F 2/2466* (2013.01); *A61F 2/013* (2013.01); *A61F 2/2418* (2013.01); *A61F 2/2439* (2013.01); *A61F 2230/0006* (2013.01); *A61F 2230/0067* (2013.01); *A61F 2230/0069* (2013.01); *A61F 2250/0069* (2013.01)

(58) Field of Classification Search
CPC ...... A61F 2/013; A61F 2/2466; A61F 2/2418; A61F 2/2439; A61F 2250/0069; A61F 2/2496; A61F 2/2442; A61F 2/2427
USPC ........................................................ 623/2.11
See application file for complete search history.

(56) References Cited

U.S. PATENT DOCUMENTS

| 2002/0058987 A1* | 5/2002 | Butaric ................... A61F 2/064 623/1.13 |
| 2004/0210304 A1 | 10/2004 | Seguin et al. |
| 2005/0119722 A1 | 6/2005 | Styrc et al. |
| 2005/0283231 A1 | 12/2005 | Haug et al. |
| 2007/0142858 A1* | 6/2007 | Bates ....................... A61F 2/013 606/200 |
| 2008/0077234 A1 | 3/2008 | Styrc |
| 2009/0299449 A1 | 12/2009 | Styrc |
| 2012/0022633 A1* | 1/2012 | Olson ................... A61F 2/2418 623/1.11 |

(Continued)

FOREIGN PATENT DOCUMENTS

| FR | 2863160 | 6/2005 |
| FR | 2 874 813 | 3/2006 |

(Continued)

*Primary Examiner* — Katrina Stransky
(74) *Attorney, Agent, or Firm* — Davidson, Davidson & Kappel, LLC (57) ABSTRACT

A device (24) for placing a seal around an implant in a blood circulation passage is provided. The device includes a hollow sheath having a longitudinal axis, and at least one releaser, deployable relative to the sheath is provided. The device (24) includes, for the or each releaser, a sealing body (64) releasably fastened on that releaser, the sealing body (64) having an angular span smaller than 360° around the longitudinal axis, and a filiform link (67) connecting at least one releaser to another releaser and/or to the controller (68) positioned in the sheath, the filiform link (67) being deformable between a relaxed idle configuration and a stretched configuration limiting the radial movement of the sealing bodies (64).

16 Claims, 6 Drawing Sheets

(56) References Cited

U.S. PATENT DOCUMENTS

2013/0310928 A1* 11/2013 Morriss ................ A61F 2/2418
623/2.12

FOREIGN PATENT DOCUMENTS

| WO | WO 2006/027499 | 3/2006 |
| WO | WO 2006/089236 | 8/2006 |
| WO | WO2006/123046 | 11/2006 |
| WO | WO 2009/044082 | 4/2009 |
| WO | WO 2011/106547 | 9/2011 |
| WO | WO 2014/056754 | 4/2014 |

* cited by examiner

DEVICE FOR PLACING A SEAL AROUND AN IMPLANT IN A BLOOD CIRCULATION PASSAGE, AND ASSOCIATED TREATMENT KIT

This claims the benefit of French Patent Application FR 14 536 99, filed Apr. 24, 2014 and hereby incorporated by reference herein.

The present invention relates to a device for placing a seal around an implant in a blood circulation passage, of the type comprising a hollow sheath having a longitudinal axis and at least one releaser, deployable relative to the sheath between a position retracted in the sheath and a position deployed outside the sheath.

This device in particular applies to the treatment of heart valves.

BACKGROUND

The heart comprises valves that are present at the outlet of the right ventricle (pulmonary and tricuspid valves) and the left ventricle (aortic and mitral valves).

These valves provide a one-way circulation of the blood flow, while avoiding blood reflux at the end of ventricular contraction.

However, diseases or malformations affect the proper operation of the valves.

In particular, the latter may suffer from calcification, thereby allowing reflux or regurgitation toward the ventricle or atrium that expelled the blood flow. The regurgitation problem leads to abnormal expansion of the ventricle, which produces heart failure over time. In some cases, the valve comprises a number of leaflets smaller than that generally observed for this type of valve, which may harm its long-term operation.

To treat this type of disease surgically, it is known to implant an endovalve between the leaflets of the diseased native valve. This endovalve comprises a tubular endoprosthesis formed by an autoextensible mesh and a flexible closer or valve most often made from an animal tissue. The flexible closer is permanently fastened in the endoprosthesis.

Such endovalves can be implanted using the endoluminal route, which considerably limits the risks associated with implantation of the valve, in particular in terms of mortality.

In some cases, the endovalves are not fully satisfactory after implantation. In fact, although the outer surface of the endoprosthesis spontaneously presses against the seat of the native valve, by pressing the leaflets between the seat and the outer surface of the endoprosthesis, leaks may remain around the outer surface of the endoprosthesis, in particular at the commissures defined between the leaflets of the native valve. These leaks occur in more than 50% of patients having undergone such an operation.

To offset this problem, a treatment device is known in the state of the art comprising an implant that can be sealably implanted in a blood flow conduit. Such sealing is provided by a sealing body able in particular to surround the commissures between the leaflets of the native valve.

However, the exact position of the commissures defined by a native valve varies from one patient to the next and the existing device does not make it possible to position the sealing bodies in those commissures in a completely satisfactory manner.

SUMMARY OF THE INVENTION

It is an object of the present invention to provide device for placing a seal making it possible to position sealing bodies in the commissures between the leaflets of a patient's native valve very precisely and in a manner suited to the structure of that patient's native valve.

A treatment device of the aforementioned type is provided, comprising:

for the or each releaser, a sealing body releasably fastened on that releaser to be released from the releaser, the sealing body having an angular span strictly smaller than 360° around a longitudinal axis; and a filiform link connecting at least one releaser to another releaser and/or to the controller positioned in the hollow sheath, the filiform link being deformable between a relaxed idle configuration and a stretched configuration limiting the radial movement away from the longitudinal axis of the sealing bodies.

According to other advantageous aspects of the invention, the device may comprise one or more of the following features, considered alone or according to all technically possible combinations:

it comprises a plurality of releasers spaced angularly apart from one another around a longitudinal axis, each releaser bearing a sealing body releasably fastened on the releaser to be released from the releaser, at least one filiform link connecting one releaser to an adjacent releaser;

it comprises at least three releasers, the device comprising a filiform link connecting each releaser to each of the adjacent releasers, the filiform links forming a peripheral chain delimiting a central space;

it comprises at least one filiform link connecting a releaser to a controller, the or each controller being inserted into the sheath independently of the or each releaser, and having a proximal end able to be manipulated by a practitioner and a distal end on which the filiform link is engaged;

the or each controller comprises a maneuvering stay that can be rotated from its proximal end, the filiform link being able to be wound on the distal end of the stay during the rotation to come transversely closer to the sealing body corresponding to the longitudinal axis;

it comprises a plurality of releasers angularly spaced apart from one another around a longitudinal axis, each releaser bearing a sealing body releasably fastened on the releaser to be released from the releaser, the controller comprising at least two maneuvering stays, each maneuvering stay being able to wind a filiform link connecting it to a releaser;

the stays are mounted telescoping in one another;

the or each controller has a loop engaged on at least one filiform link;

it comprises a plurality of releasers spaced angularly apart from one another around a longitudinal axis, each releaser supporting a sealing body releasably fastened on the releaser in order to be released from the releaser, the filiform link on which the loop is engaged connecting two releasers;

at least one filiform link is releasably connected to the controller;

the or each filiform link is formed from a silicone thread;

the or each sealing body comprises a radiopaque marker; and it comprises a filter deployable transversely around the sheath.

The invention also relates to a treatment kit for a blood circulation passage, comprising an implant designed to be implanted in a blood circulation passage and comprising an endoprosthesis deployable between a contracted state and an expanded state, the endoprosthesis advantageously bearing a valve, and a device as previously described, the or each sealing body being designed to be positioned around the implant in the blood circulation passage.

According to other advantageous aspects of the invention, the treatment kit comprises a tool for releasing the implant able to be inserted into the blood circulation passage independently of the placement device.

BRIEF DESCRIPTION OF THE DRAWINGS

The invention will be better understood upon reading the following description, provided solely as an example, and in reference to the appended drawings, in which.

DETAILED DESCRIPTION

A first treatment kit 10 for a blood circulation passage according to a first embodiment of the invention is illustrated by FIGS. 1 to 7.

Figure 7:
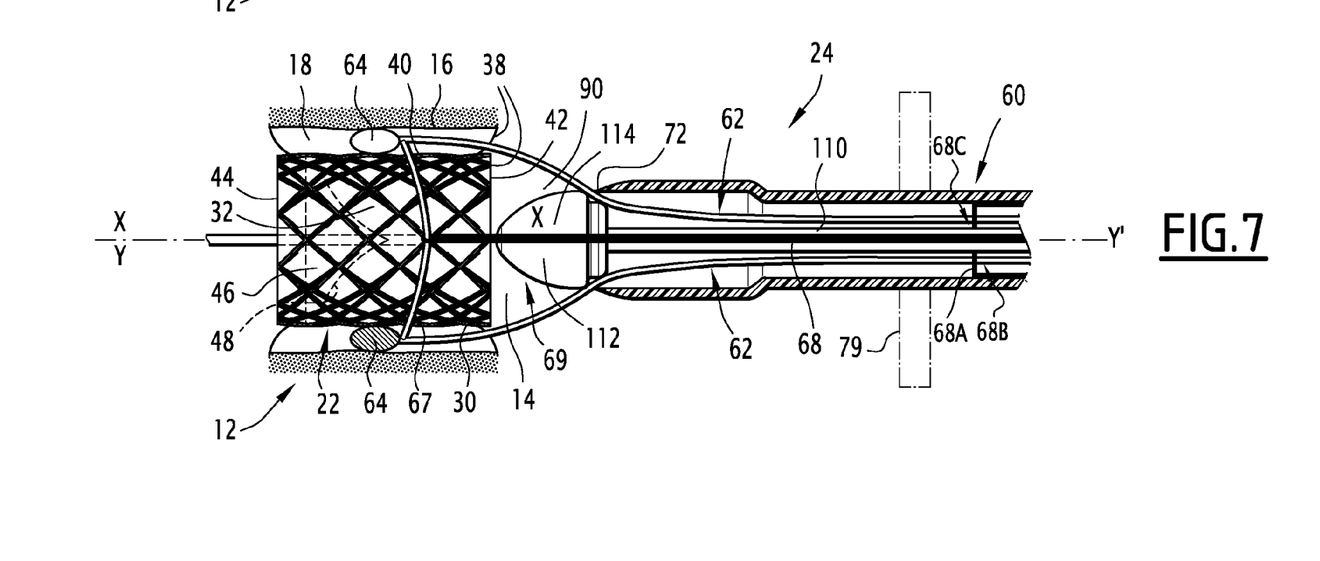
FIG. 7 is a view similar to FIG. 6, during a second step for producing the seal around an implant.
Figure 8:
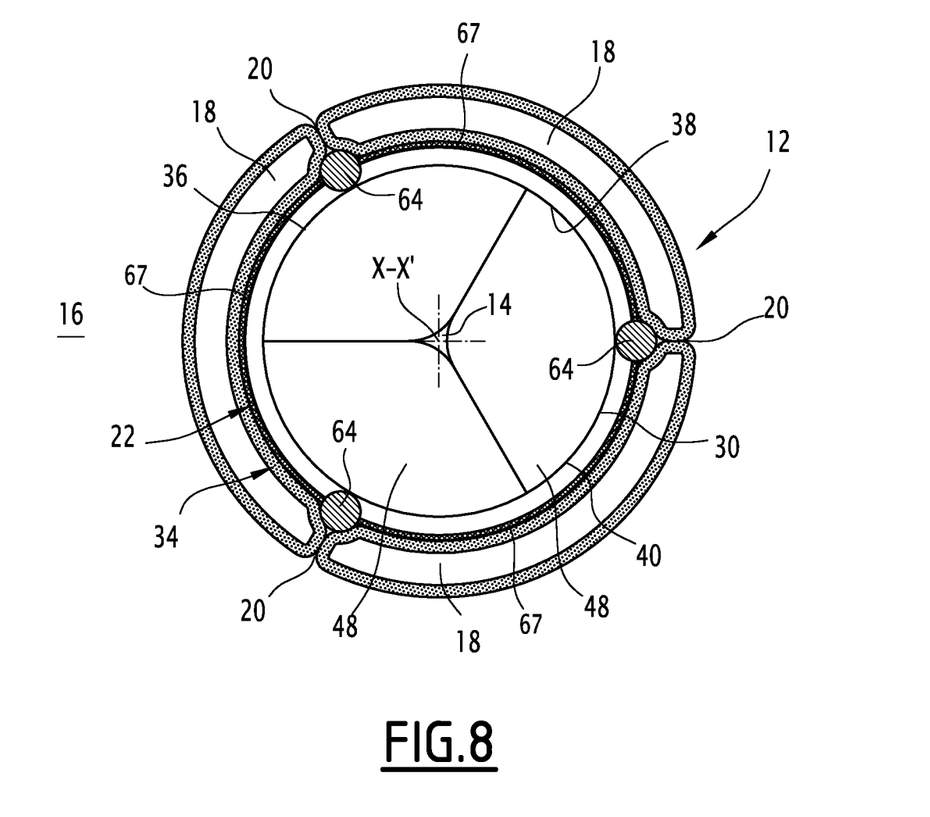
FIG. 8 is a cross-sectional view of a blood circulation passage in which an implant is implanted in a plurality of sealing bodies having been released by the device of FIG. 1.

This kit 10 is designed in particular to implant an endovalve comprising a tubular endoprosthesis endovalve, to replace a native heart valve 12, partially shown in FIGS. 7 and 8.

As illustrated in FIGS. 7 and 8, the native valve 12 is situated in a blood circulation passage 14 delimited inside a peripheral wall 16. The native valve 12 comprises a plurality of native leaflets 18 movable in the passage 14 from the wall 16.

The native valve 12 illustrated as an example in FIG. 8 comprises three native leaflets 18.

The native valve 12 delimits, between each pair of native leaflets 18, a commissure 20 situated at the junction between the native leaflets 18 at the wall 16.

The kit 10 further comprises an implant 22, shown in FIGS. 7 and 8, designed to be placed in the blood circulation passage 14, and a release tool for releasing the implant 22 into the passage 14.

The kit 10 further comprises a device 24 for placing a seal in the intermediate space situated between the implant 22 and the peripheral wall 16, around the implant 22.

In reference to FIG. 7, the implant 22 comprises an endoprosthesis 30, which advantageously forms an endovalve.

The endoprosthesis 30 has a tubular shape with axis X-X'. It delimits a central blood circulation passage 32 emerging axially on either side of the endoprosthesis 30. The endoprosthesis 30 bears a valve 34 closer attached on the endoprosthesis 30 inside the passage 32.

The endoprosthesis 30 is formed by an openworked tubular framework 36 comprising a mesh of threads that have spring properties. The framework 36 is obtained by braiding at least one thread made from stainless steel, a shape memory alloy, or a polymer. Alternatively, the framework 36 is obtained by cutting a tube, for example using a laser.

In reference to FIG. 8, the framework 36 defines an inner peripheral surface 38 and an outer peripheral surface 40. The surfaces 38 and 40 are substantially cylindrical and extend around the axis X-X' between a proximal peripheral edge 42, situated on the right in FIG. 7, and a distal peripheral edge 44, situated on the left in FIG. 7.

The inner surface 38 inwardly defines the central passage 32. The outer surface 40 is designed to be pressed at least partially against the wall 16 and/or against the leaflets 18, as will be seen below.

The framework 36 of the endoprosthesis 30 is deployable between a contracted state, in which it has a small diameter so that it may be inserted into the conduit 14, and a relaxed state, constituting its idle state, in which it has a large diameter. In the example shown in FIGS. 1 to 4, the framework 36 is spontaneously deployable between its contracted state and its expanded state. It is thus auto-expandable.

The valve 34 is for example made with a base of a native valve from an animal, such as a pig. Alternatively, it is made with a base of natural fibers such as bovine, ovine or porcine pericardium, or with a base of synthetic tissues.

Traditionally, the valve 34 comprises a tubular base 46 fastened on the inner surface 38 of the framework 36, and several flexible leaflets 48 closing off the central passage 32 that extend the base 46 downward.

The leaflets 48 are movable radially toward the axis X-X' of the passage 38 between a closing position, in which they substantially completely prevent blood from passing through the passage 32, and a position freeing the passage 32, in which they are substantially pressed against the inner surface 38 and allow blood to pass through the passage 32.

In the closed position, the leaflets 48 have a section converging toward the proximal edge 42 of the valve.

The release tool is for example the release tool described in FR-A-2,863,160, which is also published as U.S. Pub. 2005/0119722, which is incorporated by reference herein, more specifically the release tool of which is hereby incorporated by reference herein. It is able to keep the framework 36 in its contracted state when it is inserted into the blood circulation passage 14, then to deploy the framework 36 in its expanded state at its insertion point, advantageously across from the native valve 12.

Figure 1:
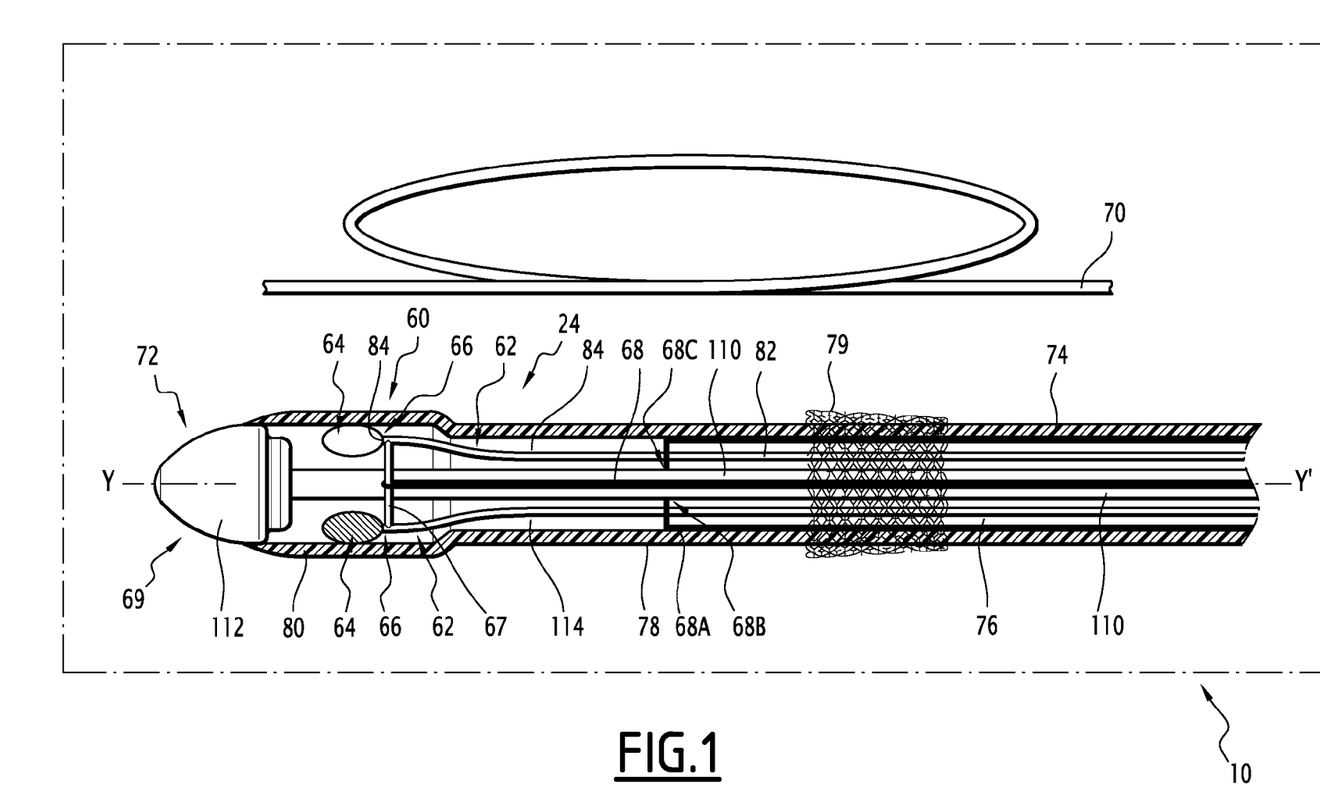
FIG. 1 is a diagrammatic partial sectional view of a treatment kit comprising a device for placing a seal according to a first embodiment of the invention.
Figure 3:
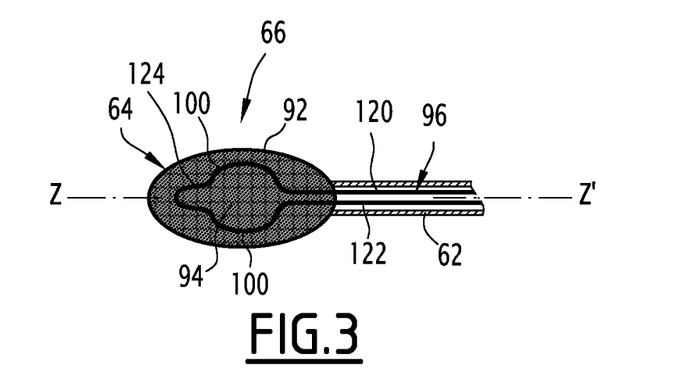
FIG. 3 is a view similar to FIG. 2, illustrating a second alternative sealing body.
Figure 4:
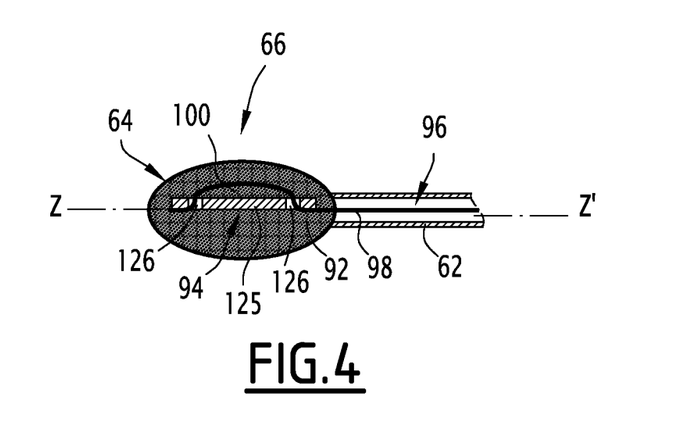
FIG. 4 is a view similar to FIG. 2, illustrating a third alternative sealing body.
Figure 5:
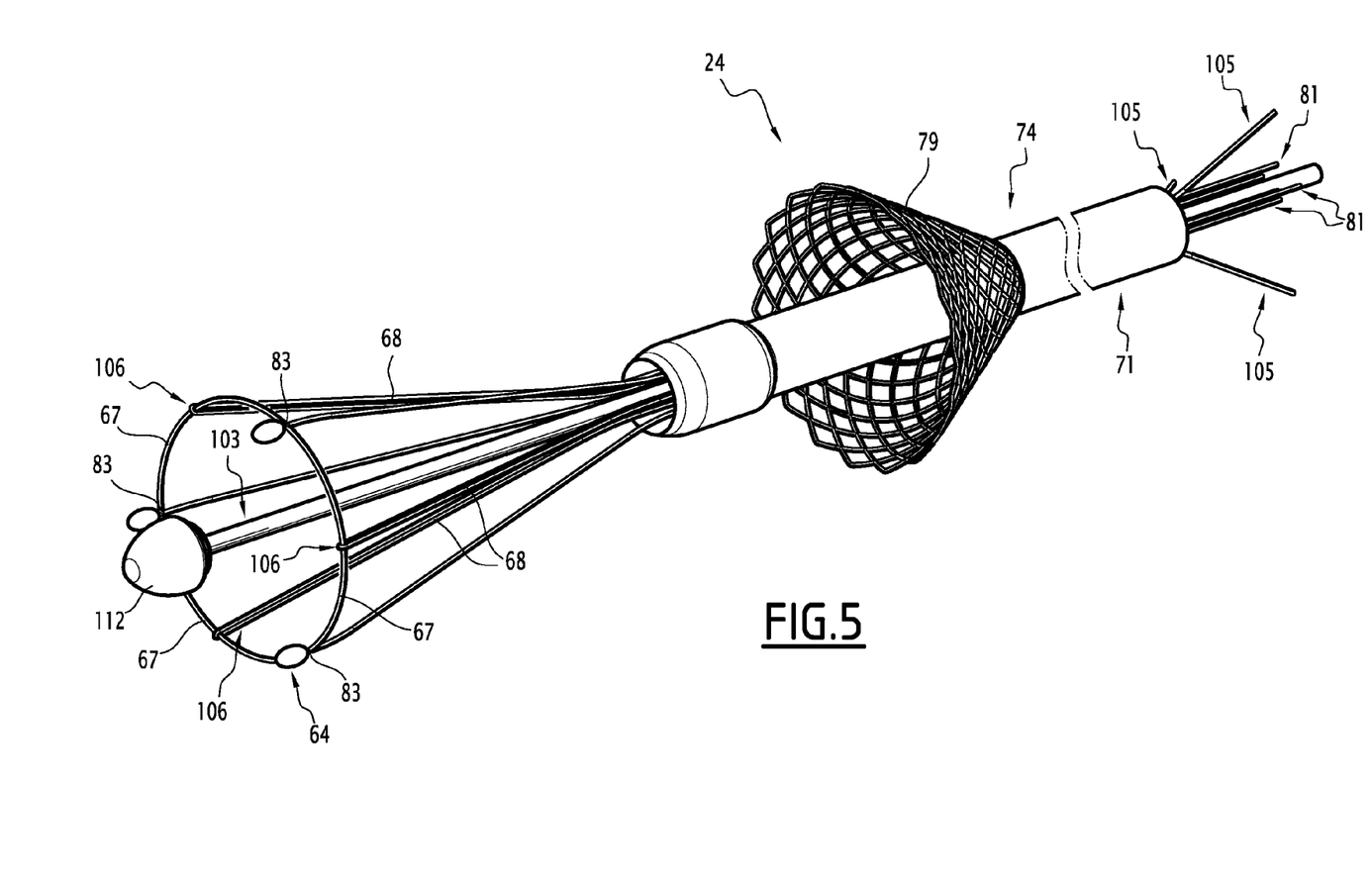
FIG. 5 is a diagrammatic perspective view of the device of FIG. 1, during a first step for producing the seal around an implant.
Figure 6:
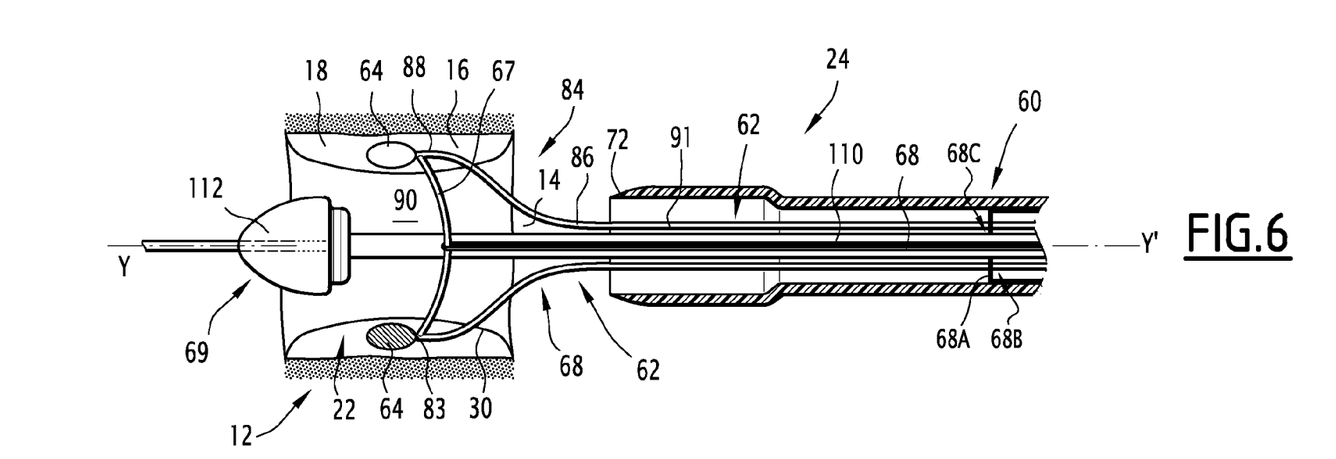
FIG. 6 is a sectional view, in a transverse plane, of a part of FIG. 5.

In reference to FIGS. 1 to 7, the placement device 24 comprises a confinement and transport sheath 60 and at least one releaser 62, mounted movably in the sheath 60 between a position retracted in the sheath 60, shown in FIG. 1, and a position removed outside the sheath 60, shown in FIGS. 5 to 7.

The placement device 24 further comprises, for each releaser 62, a sealing body 64 designed to be interposed between the implant 22 and the wall 16, and a fastener 66 for releasably fastening the sealing body 64 on the releaser 62.

The placement device 24 comprises at least one filiform link 67 designed to connect one releaser 62 to another releaser 62.

The placement device 24 further comprises at least one central controller 68 inserted into the sheath 60 independently of the releasers 62.

Each filiform link 67 is furthermore releasably connected to a central controller 68.

It comprises a substantially cylindrical inner guide 68A defining a guide passage 68B for each releaser and a circulation passage 68C for each controller 68.

The placement device 24 advantageously comprises a closer 69 for closing the sheath 60 and a surgical guide 70 for inserting and guiding the device 24 in the passage 14.

The confinement sheath 60 extends along a longitudinal axis Y-Y between the proximal end 71 shown in FIG. 5 and designed to be situated outside the patient's body, and a distal end 72, designed to be inserted into the blood circulation passage 14 up to the implantation point of the implant 22.

The sheath 60 is for example formed by a hollow tube 74 made from a flexible material. It delimits a central aperture 76 emerging at the proximal end (not visible), designed to be placed outside the patient's body, and the distal end 72, designed to be inserted into the passage 14.

In the example shown in FIG. 1, the sheath 60 comprises a tubular proximal part 78, advantageously a filter 79 mounted on a proximal part 79, and a distal capsule 80, with a transverse span larger than the transverse span of the proximal part 78.

The filter 79 is transversely deployable around the sheath 60 between a contracted state (FIG. 1) and a relaxed idle state (FIG. 5).

In the expanded state, the filter 79 has a conical shape with axis Y-Y' and the base of which is oriented toward the distal end 72 of the sheath 60. The filter 79 makes it possible to recover any calcification debris released from the native leaflets 18 during placement of the sealing bodies 64. The deployment and contraction of the filter 79 are done by deployment and contraction means that can be actuated by a practitioner outside the patient's body.

The capsule 80 receives each sealing body 64 in the retracted position of the releaser 62.

In this example, the placement device 24 comprises a plurality of independent releasers 62 each bearing a sealing body 64.

There are for example between 1 and 4 releasers 62. The releasers 62 are positioned at least partially in the inner aperture 76 of the sheath 60, while being angularly spaced apart from one another.

Each releaser 62 comprises a rod 82 extending between a proximal end 81 shown in FIG. 5 and able to be removed outside the sheath 60 to be maneuvered by a user of the device outside the patient's body, and a distal end 83 on which the sealing body 64 is fastened.

The rod 82 is self-supporting to allow a user of the device to push the sealing bodies 64 outside the sheath 60 in the passage 14, during movement of the releaser 62 from its retracted position to its deployed position.

The rod 82 is inserted into a guide passage 68B of the guide 68A.

The releaser 62 has a distal part 84 that is spontaneously deformable from a configuration radially contracted toward the axis Y-Y', which it occupies in the retracted position (see FIG. 1), and a configuration radially deployed away from the axis Y-Y', which occupies in the deployed position (see FIG. 6).

In the deployed configuration, the distal part 84 flares transversely. It has a proximal segment 86 moving away from the axis Y-Y' and a distal segment 88 parallel to the axis Y-Y' or approaching the axis Y-Y'.

The distal parts 84 of the various releasers 62 thus delimit a central space 90 between them for inserting the implant 22, thereby facilitating placement of the implant 22.

As illustrated by FIGS. 1, 5 and 6, each releaser 62 can be moved by sliding along the axis Y-Y' between the retracted position, shown in FIG. 1, and the deployed position, shown in FIGS. 5 and 6.

In the retracted position, the distal part 84 of the releaser 62 and the sealing body 64 fastened on the releaser 62 are completely received in the sheath 60, advantageously at the capsule 80.

The sheath 60 keeps the distal part 84 in its contracted configuration.

In the deployed position, the distal part 84 and the sealing body 64 have been pushed distally outside the sheath 60, past the distal end 72. The distal end 84 is in its radially deployed configuration.

Figure 2:
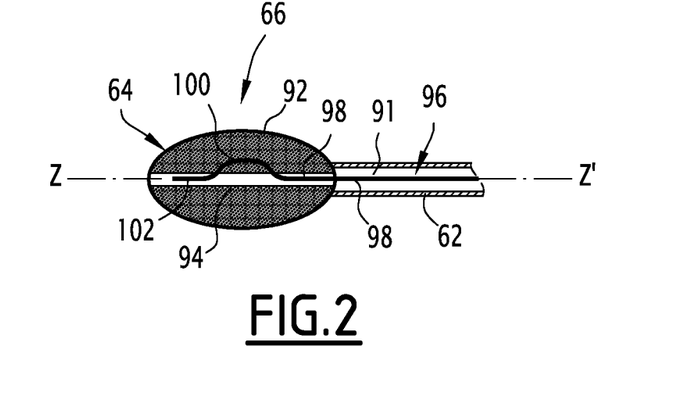
FIG. 2 is a view of a detail of the device of FIG. 1, illustrating a first alternative sealing body designed to be placed around an implant.

In the example shown in FIGS. 1 and 2, the rod 82 forming the releaser 62 is hollow. It delimits an inner circulation channel 92 for the releasable fastener 66.

In reference to FIGS. 2 and 8, each sealing body 64 has an angular span around the axis Y-Y' smaller than 360°, advantageously smaller than 180°, still more advantageously smaller than 45°.

Each sealing body 64 thus forms a periodic cushion and preferably contains a radiopaque marker.

In reference to FIG. 2, each sealing body 64 is elongated along an elongation axis Z-Z'. It is advantageously olive-shaped.

In the example of FIG. 2, the sealing body 64 comprises a block 92 of deformable material and a rigid central framework 94 positioned in the block 92.

The block 92 is for example made with a base of foam, in particular silicon or polyurethane foam. Alternatively, it is made up of discrete fabric elements housed in an outer enclosure.

In the example of FIG. 2, the framework 94 comprises a hollow central tubular membrane with axis Z-Z', around which the block 92 is positioned.

The framework 94 is made with a base of a more rigid material than the material making up the block 92.

Thus, the sealing body 64 is able to deform when it is inserted between the implant 22 and the peripheral wall 16 to hug the shape of the intermediate space between the implant 22 and the peripheral wall 16.

The sealing body 64 is releasably fastened on the distal part 84 of the releaser 62, advantageously end to end with the distal end 83.

Its elongation axis Z-Z' thus forms a small or zero angle, advantageously smaller than 30°, relative to the local axis of the distal part 84 at the point of contact with the sealing body 64.

The releasable fastener 66 in this example comprises a retainer 96 movable in the inner channel 91 and through the sealing body 64, between a configuration engaged with the sealing body 64 and a configuration releasing the sealing body 64.

In this example, the retainer 96 is formed by a pin, which advantageously extends over the entire length of the releaser 62. The retainer 96 is thus able to be manipulated by an operator of the device 24 outside the patient's body to go from its engaged configuration to its released configuration.

In the engaged configuration, shown in FIG. 2, the retainer 96 is engaged through the sealing body 64.

In the specific example shown in FIG. 2, the retainer 96 comprises, near its distal end, a proximal free segment 98 positioned in the channel 92 and the framework 94, and a radially deformed convex segment 100 that penetrates the block 92 of deformable material. It advantageously comprises a free distal end 102.

In the released configuration, the radially deformed segment 100 and the distal free segment 102 have been removed outside the sealing body 64.

In the example illustrated in FIG. 5, the placement device 24 comprises three releasers 62 and three filiform links 67 respectively connecting a pair of adjacent releasers 62.

In this example, the releasers 62 are spaced angularly apart from one another around a longitudinal axis Y-Y and each filiform link 67 connects two adjacent releasers 62 at their distal ends 83.

Thus, as shown in FIG. 5, the filiform links 67 form a peripheral chain delimiting a central space 103.

This central space 103 is able to receive the endoprosthesis 30 when all of the releasers 62 are removed from the sheath 60 and the endoprosthesis 30 is in its expanded state. Thus, the total length of all of the filiform links 67 is substantially greater than the circumference of the endoprosthesis 30 in its expanded state.

When the releasers 62 are in the retracted positions, the filiform links 67 are received in the capsule 80.

Each filiform link 67 is reversibly deformable between a relaxed idle configuration and a stretched configuration.

In reference to FIG. 5, each central controller 68 has a loop comprising a proximal end 105 and a distal end 106 on which the corresponding filiform link 67 is engaged.

Each central controller 68 is partially engaged in a circulation passage 68C of the guide 68A.

Each controller is for example formed by a thread folded into a loop at the proximal end 106.

Each proximal end 105 can be pulled by the practitioner outside the patient's body to deform the corresponding filiform link 67 from the relaxed idle configuration shown in FIGS. 1 and 5, to the stretched configuration shown in FIGS. 6 and 7.

Thus, in the stretched configuration, the filiform link 67 is able to limit the radial movement away from the longitudinal axis Y-Y' of the releasers 62 to which that link is connected.

This in particular makes it possible to limit the radial movement of the corresponding sealing bodies 64 away from the axis Y-Y' to position them precisely in the corresponding commissures.

Thus, each filiform link 67 is designed to be interposed between the implant 22 and the peripheral wall 16.

Each filiform link 67 is for example formed by a thread of silicone or any other thread made from a biocompatible material. That thread is able to remain in the patient's body after the implant 22 has been implanted.

As illustrated by FIGS. 1, 6 and 7, the closer 69 comprises a stay 110 inserted into the sheath 60, and a distal nose 112 designed to close off the sheath 60.

The stay 110 is positioned in the sheath 60 substantially at the center thereof. It delimits an annular space 114 in the inner aperture 76, that space receiving each releaser 62.

The nose 112 has a maximum transverse span greater than or equal to the maximum transverse span of the sheath 60, at the distal end 72. It has a profiled distal part to facilitate its insertion into the blood circulation passage 14.

The stay 110 and the nose 112 are inwardly delimited by an axial through passage 114, partially shown in FIG. 7, to receive the surgical guide 70.

The closer 69 is movable between a proximal position closing off the sheath 60, shown in FIG. 1, and a distal position opening the sheath 60, shown in FIG. 5.

In the proximal position, the nose 112 is placed in contact with the distal end 72 of the sheath 60 to close off the inner aperture 76. Advantageously, a proximal part of the nose 112 is inserted into the inner aperture 76, and the distal part of the nose 112 protrude outside the aperture 76.

The nose 112 thus prevents each releaser 62 from going from the retracted position to the deployed position.

In the distal position, the nose 112 is positioned axially away from the distal end 72. The stay 110 is partially deployed outside the inner aperture 76 through the distal end 72.

The inner aperture 76 emerges at the distal end 72, and the passage of each releaser 62 from the retracted position to the deployed position is possible.

Furthermore, when the closer 69 is in its distal position, and each releaser 62 is in its deployed position, the closer 69 can be moved toward an intermediate transverse separation position of each sealing body 64, shown in FIG. 6.

In this position, the nose 112 has come closer to the distal end 72 of the sheath 60. It cooperates with each releaser 62 to move transversely away from the longitudinal axis Y-Y'. This radially separates each sealing body 64.

The operation of the treatment kit 10 according to the first embodiment of the invention will now be described.

Initially, a kit 10 is provided to the practitioner. The placement device 24 is then configured so that each releaser 62 is in its position retracted in the confinement sheath 60, as illustrated by FIG. 1.

Each sealing body 64 is then fastened to the end of a releaser 62 by the releasable fastener 66. Each sealing body 64 is received in the inner aperture 76 of the sheath 60, advantageously at the capsule 80.

The filiform links 67 are in the relaxed idle position and are in the inner aperture 76 of the sheath 60, advantageously at the capsule 80.

Each filiform link 67 is engaged on the distal end 106 of a corresponding central controller 68. The distal end 106 of each central controller 68 is received in the sheath 60 at the capsule 80.

The filter 79 is in the contracted state.

The closer 69 is then in its proximal position closing off the sheath 60. The stay 110 is positioned between the releasers 62 and received in the central space 103 delimited by the filiform links 67, at the center of the sheath 60. The nose 112 closes off the distal end 72 of the sheath 60.

The practitioner then grasps the guide 70 and inserts it through the endoluminal route in the blood system up to the implantation point provided in a blood circulation passage 14.

When the implant 22 is an endovalve, the implantation point is for example situated across from a native valve 12.

Then, the practitioner slips the placement device 24 onto the surgical guide 70 and brings the device 24 to the implantation point by sliding on the guide 70.

Next, the practitioner takes the closer 69 from its proximal position to its distal position, to open the sheath 60 at the distal end 72.

Then, the practitioner removes each releaser 62 bearing a sealing body 64 outside the sheath 60. In the deployed position, the distal part 84 of each releaser 62 goes from its radially contracted configuration to its radially deployed configuration.

The filiform links 67 follow the releasers 62 in their radial expansion. The central controllers 68 in turn follow the associated filiform links 67.

During that transition, each sealing body 64 comes closer to the wall 16 delimiting the passage 14 to advantageously come into contact with that wall 16.

If the implantation point is situated in a native valve 12, the practitioner for example inserts each sealing body 64 into a commissure 20 of the valve 12 situated between two adjacent native leaflets 18.

Then, the practitioner moves the closer 69 toward the distal end 72 to reach the intermediate separated position. The nose 112 then cooperates with each releaser 62 to cause an additional radial separation of the sealing body 64 fastened on the releaser 62.

Then, the practitioner specifies the position of each sealing body 64 in the corresponding commissure 20 by pulling the proximal end 81 of the central controller 68 corresponding to that sealing body 64.

This action causes the deformation of the corresponding filiform link 67 from its relaxed idle position to its stretched position. This thereby limits the radial separation of the pair of sealing bodies 64 connected to the filiform links 67.

It is thus possible to partially retract, toward the axis Y-Y', each sealing body 64 to adjust its position relative to the commissures, by actuating an associated central controller 68, causing proximal traction on the filiform links 67 and associated radial movement of the releaser 62.

This next makes it possible to pivot the releasers 62 around the axis Y-Y', based on the patient's morphology, to ensure that the sealing body 64 is indeed placed in the desired commissure.

Then, the practitioner actuates the deployment of the filter 79 to recover any calcification debris released from the native leaflets 18.

The central space 90 situated between the releasers 62 and the central space 103 delimited by the filiform links are freed. The practitioner next inserts an additional surgical guide up to the central space 90, advantageously by a path opposite the insertion path of the guide 70.

The practitioner then guides the release tool of the implant 22 onto the additional guide and deploys the implant 22 into the central space 90, across from each sealing body 64, as illustrated by the FIG. 6.

In reference to FIG. 7, the outer peripheral surface 40 of the framework 36 then pushes each sealing body 64 radially away from the axis Y-Y' against the wall 16.

Each sealing body 64 and each filiform link 67 are therefore interposed between the implant 22 and the peripheral wall 16 in the blood circulation passage 14, to substantially plug the intermediate space present between the implant 22 and the wall 16, in particular at the commissures 20 of the native valve 12.

Then, the practitioner releases each sealing body 64 from the releaser 62 on which it is fastened. To that end, it moves the retainer 96 from its configuration engaged with the sealing body 64 to the release configuration, while keeping the sealing body 64 substantially in position by bearing on the releaser 62.

The practitioner further releases each filiform link 67 of the corresponding central controller 68.

Then, the practitioner actuates the contraction means to contract the filter 79 in its initial position.

The practitioner next retracts each releaser 62 into the sheath 60, then withdraws the sheath 60.

The device 24 allows positioning of each sealing body 64 very precisely and in a suitable manner with a variable structure of a native valve.

Furthermore, the radiopaque markers contained in the sealing bodies 64 allow the practitioner to see the position of each sealing body 64 and to correct it if needed.

In an alternative illustrated by FIG. 3, the sealing body 64 is formed by a block 92 with no central framework 94. The retainer 96 comprises two parallel strands 120, 122 folded in a loop 124 at the distal end of the retainer 96 inserted into the block 92. The loop 124 comprises two opposite deformed segments 100 protruding transversely relative to the axis Z-Z'.

The release of the sealing body 64 shown in FIG. 3 is done similarly to that described for the body 64 in FIG. 2, by pulling on the strands 120, 122 of the retainer 96 positioned channel 91.

In another alternative illustrated by FIG. 4, the central framework 94 is formed by a substantially flat member, such as an elongated disc 125. The disc 125 is provided with eyelets 126 allowing the passage of the retainer 96.

The release of the sealing body 64 shown in FIG. 4 is done similarly to that described for the body 64 of FIG. 2.

Figure 9:
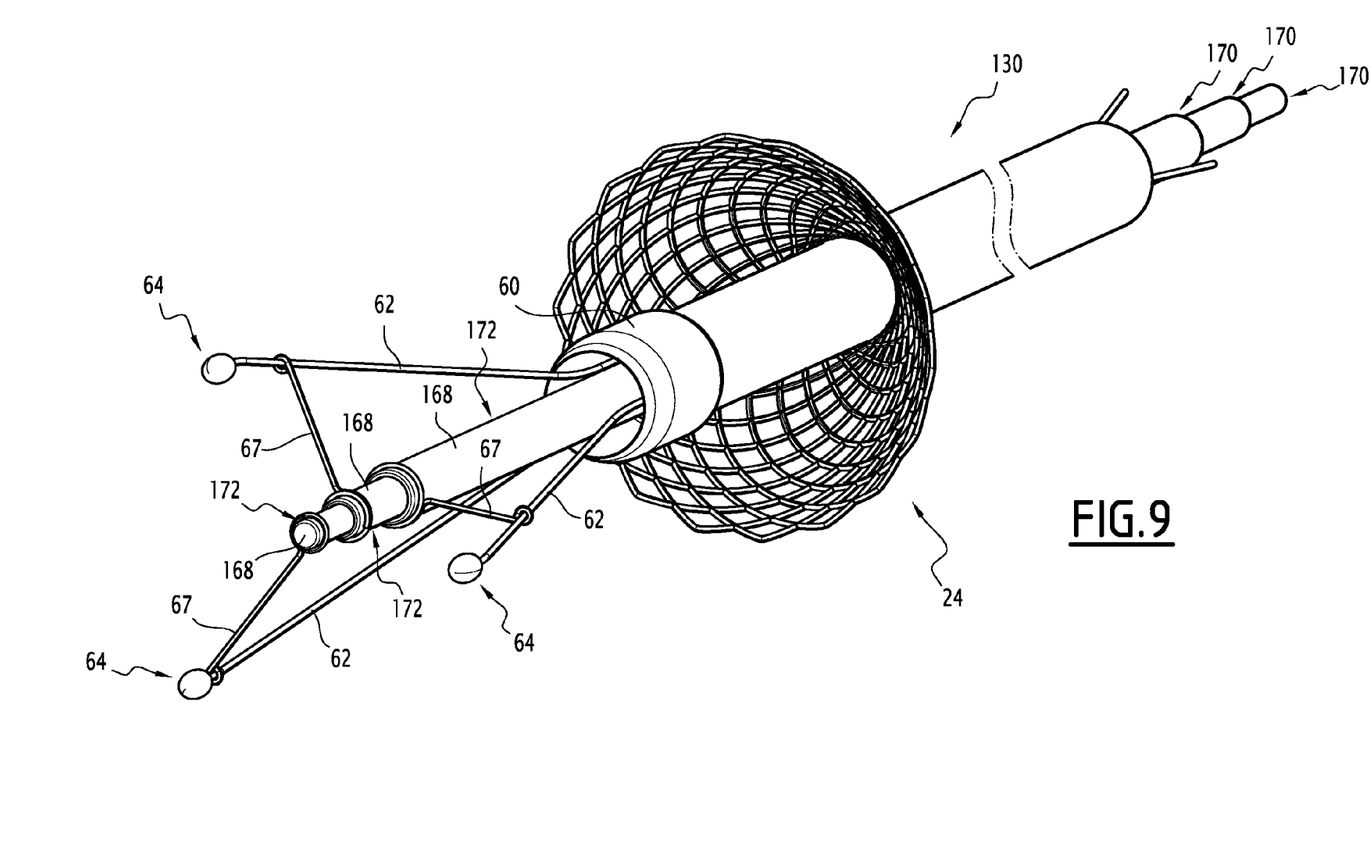
FIG. 9 is a view similar to FIG. 5 of a device for placing a seal according to a second embodiment of the invention.

The device 24 for placing a kit 130 according to a second embodiment of the invention is illustrated in FIG. 9.

Unlike the device 24 shown in FIGS. 1 to 7, the central controllers of the device 24 of FIG. 9 comprise maneuvering stays 168 inserted into the sheath 60 and mounted telescoping in one another.

Furthermore, the filiform links 67 of the device 24 of FIG. 9 connect one of the releasers 62 to one of the central controllers 168, advantageously releasably.

Each central controller 168 comprises a proximal end 170 able to be pivoted by the practitioner and a distal end 172 able to wind the corresponding filiform link 67.

Thus, the rotation of the proximal end 170 involves winding the filiform link 67 on the distal end 172 in order to deform that filiform link 67 from the relaxed idle configuration to the stretched configuration to bring the corresponding sealing body 64 transversely closer to the longitudinal axis Y-Y'.

The operation of the kit 130 according to the second embodiment of the invention differs from the operation of the kit 10 according to the first embodiment in that, in order to specify the position of each sealing body 64, the practitioner pivots the proximal end 170 of the corresponding central controller 168 to wind the filiform link on its distal end. This then makes it possible to bring the corresponding sealing body closer to the longitudinal axis Y-Y'.

What is claimed is:

1. A device for placing a seal around an implant in a blood circulation passage comprising:
   a hollow sheath having a longitudinal axis;
   one or more releasers deployable relative to the sheath between a position retracted in the sheath and a position deployed outside the sheath;
   for the or each releaser, a sealing body releasably fastened on the corresponding releaser to be released from the releaser, the sealing body having an angular span strictly smaller than 360° around a longitudinal axis; and
   at least one filiform link connecting at least one of the releasers to another releaser and/or to a controller positioned in the hollow sheath, the filiform link being deformable between a relaxed idle configuration and a stretched configuration limiting the radial movement away from the longitudinal axis of the sealing bodies, the or each sealing body and the or each filiform link being movable in the blood circulation passage independently from the implant.

2. The device as recited in claim 1 wherein the at least one releaser is a plurality of releasers spaced angularly apart from one another around a longitudinal axis, each releaser bearing one of the sealing bodies releasably fastened on the releaser to be released from the releaser, the at least one filiform link connecting one of the releasers to an adjacent one of the releasers.

3. The device as recited in claim 2 wherein the at least one releaser is at least three releasers, the at least one filiform link being a plurality of filiform links, each of the filiform links connecting each releaser to each of the adjacent releasers, the filiform links forming a peripheral chain delimiting a central space.

4. The device as recited in claim 1 wherein the at least one filiform link connects one of the releasers to at least one controller, the or each controller being inserted into the sheath independently of the or each releaser, the or each controller having a proximal end able to be manipulated by a practitioner and a distal end on which the at least one filiform link is engaged.

5. The device as recited in claim 4 wherein the or each controller comprises at least one maneuvering stay able to be rotated from a proximal end of the stay, the at least one filiform link being able to be wound on a distal end of the stay during the rotation to come transversely closer to the sealing body corresponding to the longitudinal axis.

6. The device as recited in claim 5 wherein the one or more releasers is a plurality of releasers spaced angularly apart from one another around a longitudinal axis, each releaser bearing one of the sealing bodies releasably fastened on the releaser to be released from the releaser, the at least one maneuvering stay being at least two maneuvering stays, each maneuvering stay being able to wind one of the filiform links connecting the maneuvering stay to one of the releasers.

7. The device as recited in claim 6 wherein the stays are mounted telescoping in one another.

8. The device as recited in claim 4 wherein the or each controller has a loop engaged on the at least one filiform link.

9. The device as recited in claim 8 wherein the one or more releasers is a plurality of releasers spaced angularly apart from one another around the longitudinal axis, each releaser supporting one of the sealing bodies releasably fastened on the releaser in order to be released from the releaser, the filiform link on which the loop is engaged connecting two of the releasers.

10. The device as recited in claim 4 wherein the at least one filiform link is releasably connected to the at least one controller.

11. The device as recited in claim 1 wherein the or each filiform link is formed from a silicone thread.

12. The device as recited in claim 1 wherein the or each sealing body comprises a radiopaque marker.

13. The device as recited in claim 1 further comprising a filter deployable transversely around the sheath.

14. A treatment kit for a blood circulation passage comprising:
    an implant designed to be implanted in a blood circulation passage and comprising an endoprosthesis deployable between a contracted state and an expanded state, the endoprosthesis advantageously bearing a valve;
    the device as recited in claim 1, the or each sealing body being designed to be positioned around the implant in the blood circulation passage.

15. The treatment kit as recited in claim 14 further comprising a release tool for releasing the implant able to be inserted into the blood circulation passage independently of the placement device.

16. The treatment kit as recited in claim 14 wherein the endoprosthesis bears a valve.

\* \* \* \* \*